(12) United States Patent
Vojnovic et al.

(10) Patent No.: US 6,531,097 B1
(45) Date of Patent: Mar. 11, 2003

(54) MEASURING THE CONCENTRATION OF A SUBSTANCE

(75) Inventors: Borivoj Vojnovic, London (GB); William K. Young, Hertfordshire (GB); Peter Wardman, Bucks (GB)

(73) Assignee: Cancer Research Campaign Technology, Ltd., London (GB)

( * ) Notice: Subject to any disclaimer, the term of this patent is extended or adjusted under 35 U.S.C. 154(b) by 0 days.

(21) Appl. No.: 09/559,780

(22) Filed: Apr. 27, 2000

Related U.S. Application Data

(63) Continuation of application No. PCT/GB98/01809, filed on Jun. 19, 1998.

(30) Foreign Application Priority Data

Nov. 3, 1997 (GB) ................................................ 9723229

(51) Int. Cl.⁷ .............................................. G01N 21/64
(52) U.S. Cl. ..................... 422/82.07; 422/55; 422/83; 422/85; 422/68.1; 422/82.08; 436/172
(58) Field of Search ............................. 422/55, 83, 85, 422/82.07, 82.08, 68.1; 436/172

(56) References Cited

U.S. PATENT DOCUMENTS

| 4,557,900 A | 12/1985 | Heitzmann |
| 5,043,285 A | 8/1991 | Surgi |
| 5,173,432 A | 12/1992 | Lefkowitz et al. |
| 5,304,809 A | 4/1994 | Wickersheim |
| 5,351,268 A | 9/1994 | Jensen et al. |

FOREIGN PATENT DOCUMENTS

| EP | 0252578 A2 | 1/1988 |
| EP | 0329297 A2 | 8/1989 |
| EP | 0442060 A2 | 8/1991 |
| GB | 2265709 | 10/1993 |
| WO | WO94/10553 | 5/1994 |

OTHER PUBLICATIONS

W.K. Young et al., *Measurement of Oxygen Tension in Tumours by Time–Resolved Fluorescence* British Journal of Cancer (1996) 74 (Suppl. XXVII), pp. S256–S259.

D.R. Collingridge et al., *Measurement of Tumor Oxygenation: A Comparison Between Polarographic Needle Electrodes and a Time–Resolved Luminescence–Based Optical Sensor*, Radiation Research 147, pp. 329–334 (1997).

Primary Examiner—Jill Warden
Assistant Examiner—Sam P. Siefke
(74) Attorney, Agent, or Firm—Burns, Doane, Swecker & Mathis, L.L.P.

(57) ABSTRACT

A system for measuring the concentration of an assay substance comprising a sensor having an optical fiber (10) on one end of which is coated a body (22). A fluorophor is dispersed within the body (22), the fluorescent activity of which is altered in relationship to the concentration of the assay substance. Light from a source such as an LED (40) is carried by the fiber (10) to the body (22). Light emitted by the fluorophor is carried to a detector unit (54) along the fiber (10). Concentration of the assay substance is determined by measurement of the characteristics of the growth in emitted light following activation of the LED (40).

32 Claims, 5 Drawing Sheets

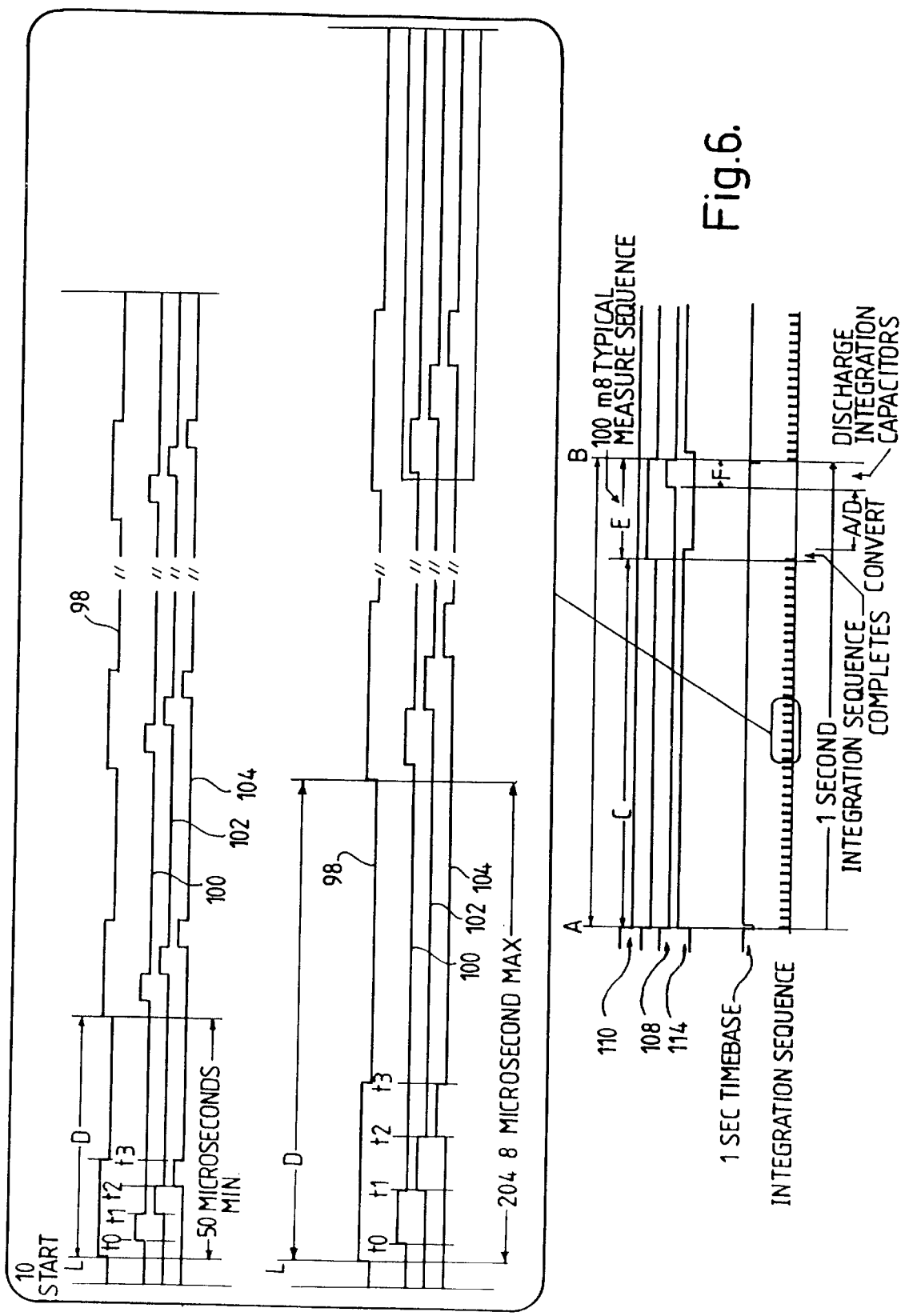

MEASURING THE CONCENTRATION OF A SUBSTANCE

RELATED APPLICATIONS

This application is a Continuation of International application PCT/GB98/01809 designating the US filed Jun. 19, 1998 and claims the priority of UK application GB9723229.2 filed Nov. 3, 1997, both of which application are incorported herein by reference in their entirety.

FIELD OF THE INVENTION

The present invention relates to an apparatus and a method for determining the concentration of a substance. In one particular application, the invention relates to apparatus and a method for determining the concentration of oxygen within living tissue cells.

BACKGROUND TO THE INVENTION

For clarity, the term "assay substance" will be used in this specification to refer to the particular substance that an apparatus or method according to the invention is intended to detect.

It is well-known that a large number of fluorescent dyes measurably change their fluorescing characteristics in dependance upon the concentration of specific substances. For example, it is known that the fluorescence of the fluorophor tris(4,7-diphenyl-1,10-phenanthroline) ruthenium chloride is decreased in an inverse relationship to concentration of oxygen. It is recognised that both the intensity and the duration of light emitted by fluorescence of this substance are reduced in the presence of oxygen.

This phenomenon has been applied in measurement of oxygen tension in tumours, for example, as disclosed in the paper of W. K. Young, B. Vojnovic and P. Wardman: "Measurement of oxygen tension in tumours by time-resolved fluorescence" British Journal of Cancer (1996) 74 (Supl.XXVII) S256–S259. In this disclosure, apparatus for measuring oxygen tension comprises a sensor in which a fluorophor is localised in a polymer and coated on an end surface of an optical fibre. A pulsed laser is used to apply pumping light to the fibre, which light is transmitted to the fluorophor. Following the pulse, the fluorophor emits light, which travels back along the fibre to a detector. An assessment of the concentration of oxygen present is made on the basis of the time taken for the fluorescent emission to decay, the rate of decay increasing with the concentration. This sensor is advantageous in that it is relatively unreactive with biological tissue and will not affect living cells even after a prolonged contact with them, and in that it does not consume oxygen during detection.

The operation of such apparatus is, to a large extent, satisfactory. However, the apparatus does have a major disadvantage. In order to generate fluorescence of sufficient intensity to be measurable, a high-intensity light source is needed. In practice, it has been found that a laser source is required. While laser sources are readily available, they are relatively costly, such that they represent a significant portion of the total cost of a sensor.

SUMMARY OF THE INVENTION

It is an aim of the invention to provide a system for detecting the concentration of an assay substance which has all of the advantages of the above-described prior art system, but which does not require use of a laser light source.

According to a first of its aspects, the invention provides a sensor for detecting concentration of an assay substance comprising an optical fibre having an end surface on which is disposed a polymer body within which a multiplicity of particles is immobilised, on which particles is adsorbed a fluorophor, the polymer being such as to allow the assay substance to permeate into the body to come into contact with the fluorophor, and the fluorophor being selected as having a fluorescent activity which is measurably altered in the presence of the assay substance.

It has been found that the pattern of distribution of the fluorophor in a sensor embodying the invention is particularly effective in transmitting a high proportion of the light generated by the fluorophor back along the fibre for detection.

Preferably, the sensor comprises a single optical fibre which carries light from a pumping light source to the polymer body and which carries light emitted by the fluorophor from the polymer body to a detector. This further simplifies the construction of the sensor.

It has been found to be advantageous for the numeric aperture of the optical fibre to be greater than 0.3, and, in some embodiments, yet more advantageous to be greater than 0.4. In particularly preferred embodiments, a numerical aperture on the range 0.45 to 0.5 is selected. Numerical apertures in these ranges are particularly suited to collection of light from the fluorophor in the body of active material.

An optical fibre for use in a sensor embodying the invention is advantageously of less than 300 $\mu$m in diameter. A diameter of approximately 200 $\mu$m has been found to be particularly suitable.

The particles may suitably be silica gel particles. It is generally preferable for such particles to be of as small a size as possible, since this maximises the surface area on which dye can be adsorbed and also promotes cross-linking of the polymer matrix. At present, silica particles having an average diameter of 5 $\mu$m are readily available. It is preferable that the silica particles are of an average diameter of 5 $\mu$m or less.

In a particularly useful embodiment of the invention, the assay substance is oxygen. In such embodiments, a suitable polymer is a silicone rubber. A suitable fluorophor for use in such embodiments is a ruthenium complex dye, for example tris(4,7-diphenyl-1,10-phenanthroline). However, many other dyes could also be used, a prime desirable property being that the dye has a relatively long fluorescent lifetime; preferably in the order of several $\mu$s when unquenched by the assay substance.

In principle, a dye with a short fluorescent lifetime could be used. If this is the case, a correspondingly fast light source must be used to excite the fluorophor, and the light source must be controlled by suitably fast switching circuitry.

From another of its aspects, the invention provides a method of making a sensor for measuring the concentration of an assay substance in which a fluorescent dye is adsorbed onto a multiplicity of solid particles, subsequently dispersing the particles in a liquid polymer, applying the liquid polymer and the particles contained in it to an end surface of an optical fibre, and curing the liquid polymer to form a polymer body on the end surface of the optical fibre, the dye having been selected as to have a fluorescent activity which is measurably altered in the presence of the assay substance, and the polymer having been selected to be permeable to the assay surface when in its cured condition.

In such methods, the optical fibre typically comprises a core, a cladding, and a protective buffer coating which covers the cladding. In such cases, the method includes removal of the buffer coating from an end portion of the fibre prior to application of the liquid polymer, and subsequent to curing of the liquid polymer, a protective coating is applied to cover the said end portion and the polymer body. In such embodiments, the protective coating may be formed from the same liquid polymer as is applied to the end portion of the fibre. The polymer of the protective coating may be substantially pure or it may incorporate opaque particles such as carbon black. This latter arrangement isolates the fluorophor from ambient light, while the former arrangement may offer greater acceptability for use in contact with biological tissue.

Alternatively, the method may include insertion of the said end portion through a hollow member, such that its end face, on which the liquid polymer is applied, projects from the hollow member, and subsequent to curing of the polymer layer, a protective coating is applied to cover an end face of the tubular member and the polymer body. The hollow member may be a hollow needle made, for example, from steel or a ceramic material. The arrangement described in this paragraph has the advantage of having high mechanical durability.

In a third of its aspects, the invention provides a system for measuring the concentration of an assay substance comprising:
  a sensor having a sensing body including fluorophor, which fluorophor has a fluorescent activity which is measurably altered in relation the concentration of the assay substance and light conveying means for conveying light to and from the fluorophor;
  a pumping light source which, in operation, applies light to the light conveying means to activate the fluorophor;
  a detector for detecting light emitted by the fluorophor in the polymer body and for generating a signal in response thereto;
  analysing apparatus for analysing the signal generated by the detector, and calculating from that signal the concentration of assay substance detected by the sensor; characterised in that
    the detector operates to detect transient change in light emitted by the fluorophor simultaneously with the pumping light source operating to apply light to the optical fibre.

This system is particularly advantageous because operation of the light source simultaneously with the detector results in a substantially greater amount of fluorescent light output, than would occur with a pulsed source of an equivalent brightness operated briefly before operation of the detector. By virtue of this, the light source may be a source other than a laser, for example, one or more light emitting diodes.

A system according to this aspect of the invention may operate by analysing the change in the light emitted by the fluorophor which occurs after the light source starts to operate. As such, the system analyses the kinetics of the growth in light output which takes place in response to operation of the light source. In such a system, it is normal to operate the light source for a time which is substantially larger than the time during which light emitted by the fluorophor changes following the start of operation of the light source.

In most practical embodiments, the light source is operated repeatedly, the analysing means being operable to calculate an average value of a plurality of calculated concentration values. This arrangement ensures that random variations in any one measurement do not substantially affect the accuracy of the system.

It is preferable in a system according to this aspect of the invention for the sensor to have a single optical fibre through which light is transmitted to the fluorophor, and through which light from the fluorophor is returned to the detector. In such embodiments, the system typically further comprises an optical means, such as beam splitter, to split light emerging from the optical fibre from light which is entering the fibre from the light source.

In another of its aspects, the invention provides an analysis system for calculating a lifetime period of an exponentially varying signal comprising:
  three or more integrating circuits, each having an input for receiving the signal an output on which is generated a signal representative of the value of the input signal integrated over time;
  for each integrator, a switch circuit having a control input and operative to selectively connect or disconnect the input of the associated integrator to the signal in dependance upon the state of its control input;
  timing means responsive to commencement of exponential variation of the signal, and operative to generate control signals for application to the control inputs of the switch circuits, the control signals being timed such that the three switches connect their respective integrating circuits, in turn, to the signal for three equal and consecutive time periods during exponential change of the signal; and
  computing means operative to receive output signals from the integrating circuits, and perform on them analysis whereby the lifetime value of the exponential change can be determined.

This system is particularly useful in systems of the above defined aspects of the invention, but can also find application in other systems in which high-speed analysis of exponentially varying signals is needed. Its particular advantage is that the mathematically difficult task of performing the integration is carried out in high-speed, low-cost dedicated hardware. The computing means can therefore be of relatively low performance, since it need perform only a few mathematically simple operations.

The integrating circuits can conveniently be implemented as operational amplifier integrators.

It may be that alternative faster integrating circuits would be required if a dye of relatively short fluorescent lifetime is used.

The computing means will typically comprise a digital computer, with a suitable analogue-to-digital conversion circuit being provided between the integrating circuits and the computing means. In particularly convenient embodiments, the computing means comprises a general-purpose, microprocessor-based computer, such as a desktop personal computer.

An embodiment of the invention will now be described in detail, by way of example, and with reference to the accompanying drawings.

BRIEF DESCRIPTION OF THE DRAWINGS

FIG. 6 is a diagram showing the relative timing of signals within the system (the horizontal time axis being not to scale)

DESCRIPTION OF THE EMBODIMENTS

Figure 1:
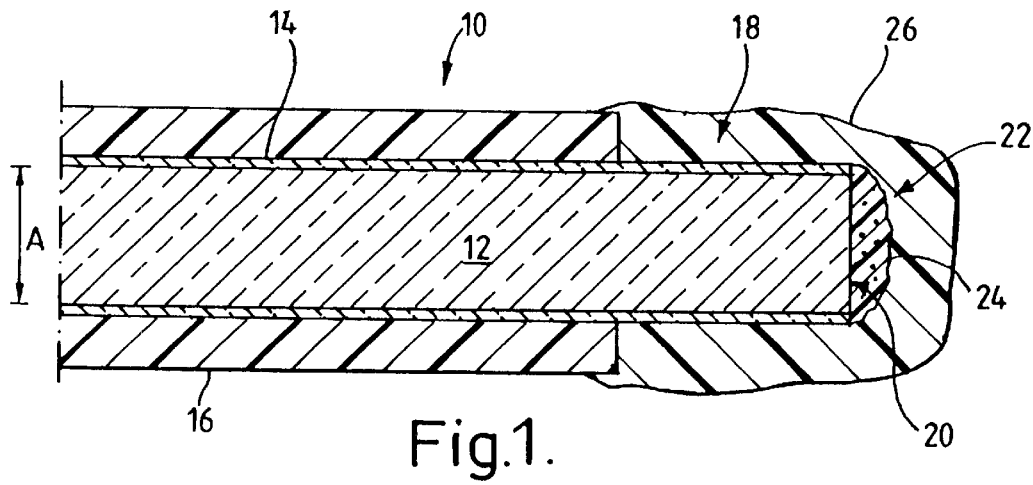
FIG. 1 is a cross-sectional view of a sensor for use in apparatus embodying the invention.
Figure 2:
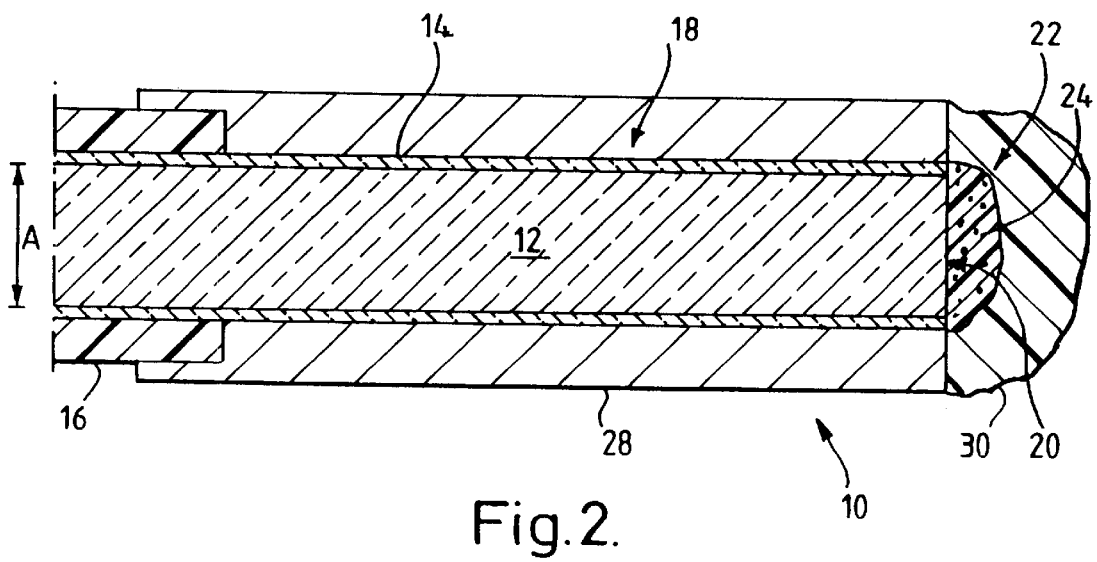
FIG. 2 is an alternative sensor to that shown in FIG. 1.

With reference to FIGS. 1 and 2, there is shown two alternative sensor arrangements which embody, or form part of various aspects of the invention.

The sensor 10 comprises an optical fibre which is formed from a light transmitting core 12 surrounded by a cladding 14. A protective buffer layer 16 surrounds the cladding 14 to give the fibre mechanical strength and robustness.

The diameter of the fibre, shown at dimension A, is approximately 200 $\mu$m. For this exemplary embodiment, the particular fibre chosen was a TECS (t.m.) optical fibre manufactured by 3M (t.m.).

The fibre has an end surface 20. An end portion of the fibre 18, extending from the end surface 20, is bared of the buffer layer 16. On the end surface 20, there is formed a body 22. The body comprises a quantity of moulded polymer formed as a curved projection from the end surface 20. Within the body 22, a multiplicity of particles 24 are dispersed.

Each of the particles 24 is formed from silica gel. The average diameter of the particles is approximately 5 $\mu$m. A fluorescent dye—tris(4,7-diphenyl-1,10-phenanthroline)Ru(II)Cl is adsorbed on the surface of the silica gel particles prior to their being incorporated into the body. In this way, the dye is immobilised within the body 22.

In a first arrangement of the sensor, the end portion 18 and the body 22 are covered in a moulded protective coating 26 of the same polymer as forms the body in a pure form (that is, containing no silica particles). The protective coating 26 serves to provide mechanical protection for the body 22 and isolates it from the clinical environment in which it will be used. In an alternative arrangement shown in FIG. 2, the end portion 18 is inserted into a tubular rigid needle 28 which has a central axial through bore. The needle 28 is arranged such that the end surface 20 of the fibre is disposed substantially at a free open end of the bore. A protective coating 30 is applied to cover the body 22 and a surrounding end surface of the needle 28. The needle 28 is also sealed to the buffer layer 16. By providing such a rigid needle 28, there is produced a sensor which has a robust sensing tip. The needle may be made of steel, other metal, ceramic, or other materials. This has little bearing on the operation of the sensor. However, in some embodiments, such as within a magnetic resonance imaging scanner, the presence of a magnetic or conductive probe may be undesirable. Alternatively, the end of the fibre may be enclosed within the bore of the needle.

For reference now to FIG. 3, a system which incorporates the sensor of FIG. 1 or FIG. 2 will now be described.

Figure 3:
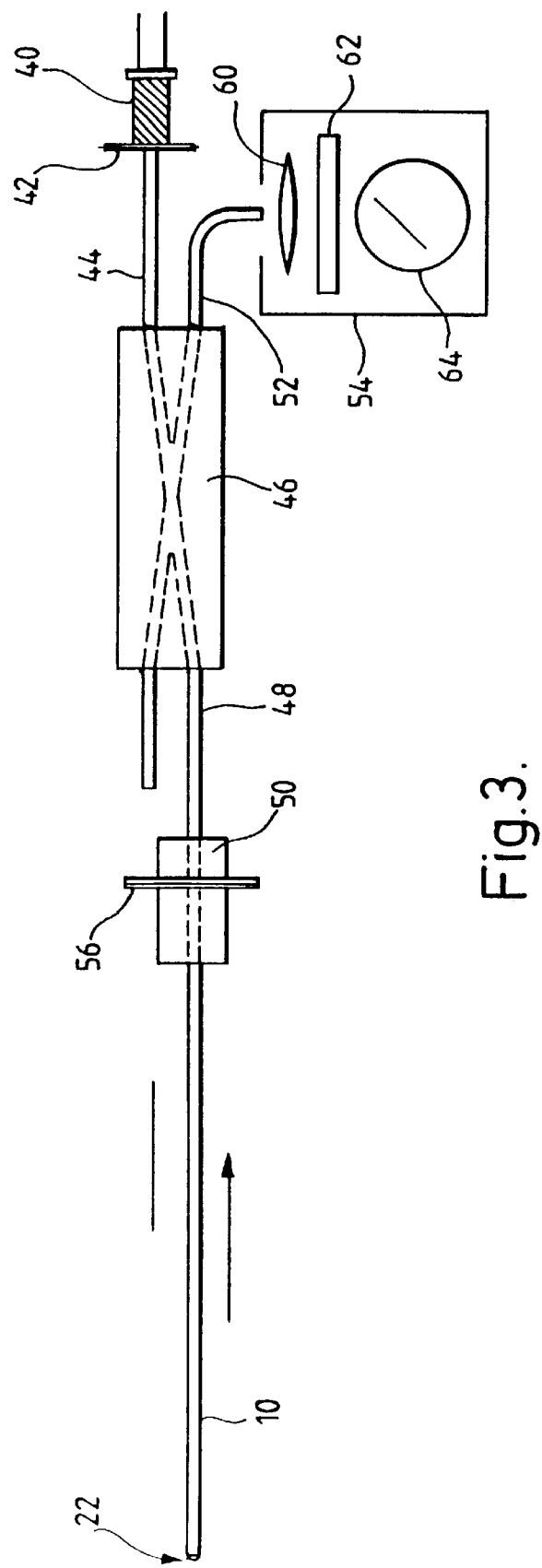
FIG. 3 is a schematic diagram of a sensing apparatus embodying the invention.

An overview of the system is shown in FIG. 3. The system comprises a light source constituted by a light emitting diode (LED) 40. The light from the LED 40 passes through a 450 nm acetate filter 42 to pass into a first optical fibre 44.

A y-beam splitter is formed by a 2×2 splitter 46, one port of which is unused. A first optical fibre 44 is connected to a first port on a first side of the splitter 46. A second optical fibre 48 is connected to a port on the second side of the splitter 46 such that light entering the splitter 46 through the first optical fibre 44 is transmitted to the second optical fibre 48. The second optical fibre 48 connects the splitter 46 to a coupler 50. A third optical fibre 52 is connected to a second port on the first side of the slitter 46. The third optical fibre 52 connects the splitter 46 to a detector unit 54, which will be described in more detail below.

The LED 40, the splitter 46 and the detector unit 54 are all disposed within a common housing. The coupler 50 permits optical connection of a fibre external of the housing, through a wall 56, to the second optical fibre 48. In this case, a sensor 10, as described with reference to FIG. 1 or FIG. 2, is connected to the coupler 50.

In use, light is emitted from the LED 40, passes through the acetate filter 42, into the first optical fibre 44. From there, it passes through the splitter 46 into the second optical fibre 48, and then through the coupler 50, into the sensor 10. This light causes fluorescent activity within the body 22 on the end surface of the sensor 10. Such fluorescent activity causes light to be produced with an emission spectrum peaking at around 600 nm. This light travels from the sensor 10, through the coupler 50, into the second optical fibre 48. It then passes through the splitter 46 and into the third optical fibre 52, to be carried to the detector unit 54.

The detector unit 54 comprises a coupling lens 60, a 590 nm long-pass filter 62 and a photomultiplier tube 64. Light from the third optical fibre 52 is received by the coupling lens 60, passes through the filter 62 to be received by the photomultiplier tube 64. The photomultiplier tube 64 generates an electrical output signal which is proportional to the amount of light which it receives. The apparatus and method for processing this signal will be described below.

Figure 4:
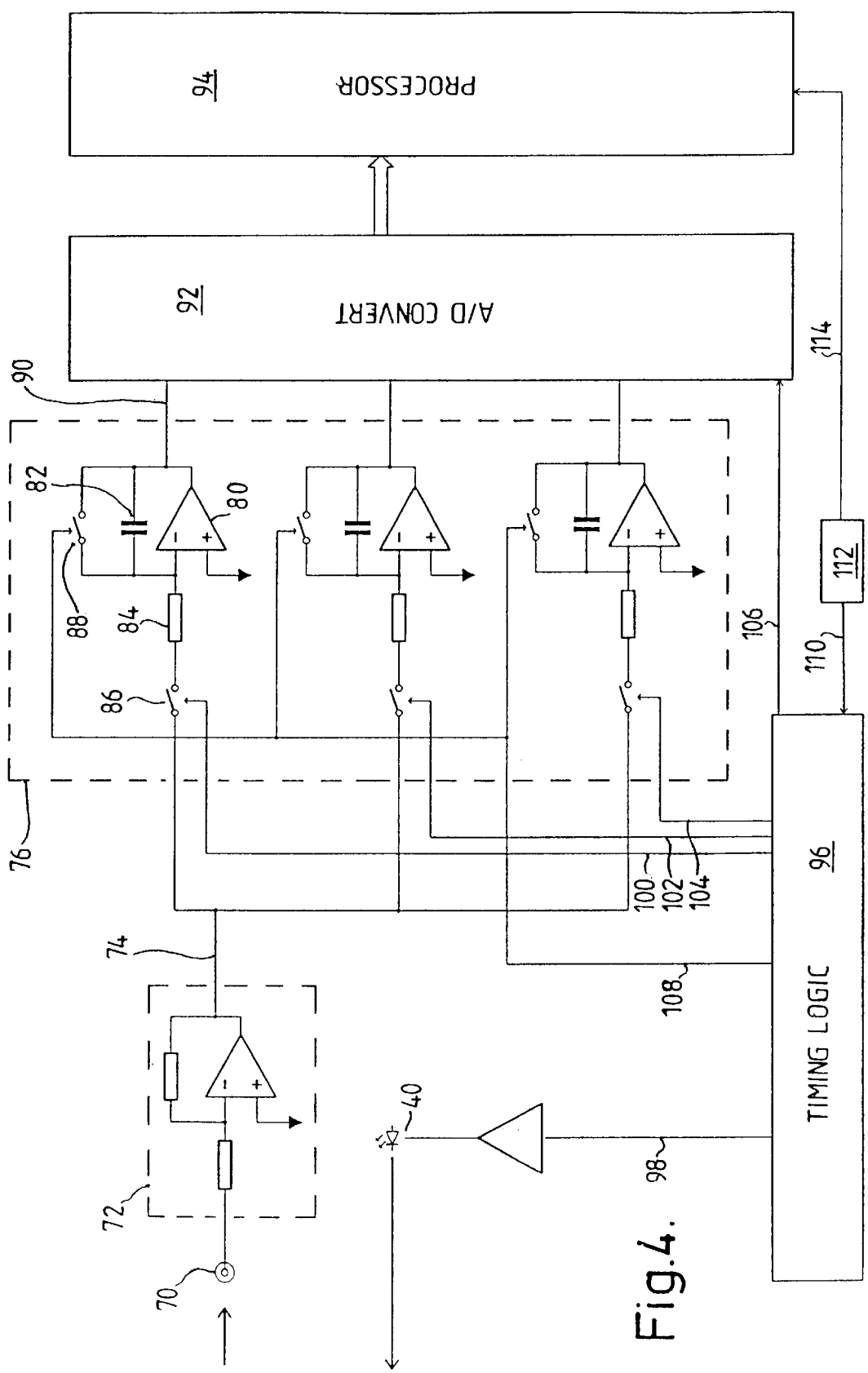
FIG. 4 is an overview of the signal processing circuit construction of apparatus embodying the invention.

With reference to FIG. 4, the electrical signal from the photomultiplier tube 64 is received into the signal processing circuits at a connector 70.

The first stage of processing the signal fed to the connector is carried out by an amplifier stage 72. The amplifier stage comprises an operational amplifier connected as an inverting DC amplifier. The output of the amplifier stage at 74 is a signal with a voltage proportional to the amount of light being received by the photomultiplier tube 64.

The output from the amplifier stage is fed to an input of an integrating stage 76. The integrating stage 76 comprises three identical integrating channels, each of which comprises a conventionally designed operational amplifier integration circuit comprising an operational amplifier 80 with a capacitor 82 connected between its output and its non-inverting input. The inverting input of the operational amplifier 80 is grounded. The integrating circuit has a series resistor 84 on its input.

The integrating stage 76 further comprises three high-speed electronic channel switches 86. Each switch 86 connects a respective one of the integrating channels to the input of the integrating stage 76. A respective electronic resetting switch 88 is also connected across each of the capacitors 82 to permit discharge of the capacitor 82 to reset the integrating circuit between integration operations.

The integrating stage 76 has three outputs 90, each connected to the output of a respective one of the integration channels.

The outputs 90 of the integration stage 76 are each connected to a respective input of a multi-channel analogue-to-digital (A/D) converter 92. The A/D converter 92 generates a digital output signal which is fed to a computer 94 for processing.

The above described circuit is controlled by a timing stage 96. The timing stage 96 has an output 98 to control the LED 40, outputs 100, 102, 104 each of which controls a respective one of the electronic channel switches 86, a control output 106 for controlling operation of the A/D converter 92 and a reset output 108 which simultaneously actuates the three resetting switches 88. The timing stage also has a start triggering input line 110.

A system control circuit 112 is provided to initiate operation of the timing stage 96 through the triggering input line. The system control circuit 112 also controls operation of the computer through an interrupt line 114.

Having described the apparatus of the present invention, it is now appropriate to describe the principles behind its operation, and, subsequent to that, its method of operation.

Immediately after the LED 40 starts to operate, the fluorophor in the sensor 10 begins to fluoresce. An oxygen-dependant component of the amount of light being emitted by such fluorescence grows exponentially to a steady maximum value within a few µs. In a system such as this, a lifetime value T for the exponential growth varies in dependance upon the degree of fluorescent activity in the sensor 10. Since the fluorescent activity is determined by the concentration of oxygen at the probe tip, if the value of τ can be determined, the concentration of oxygen can then be found.

Figure 5:
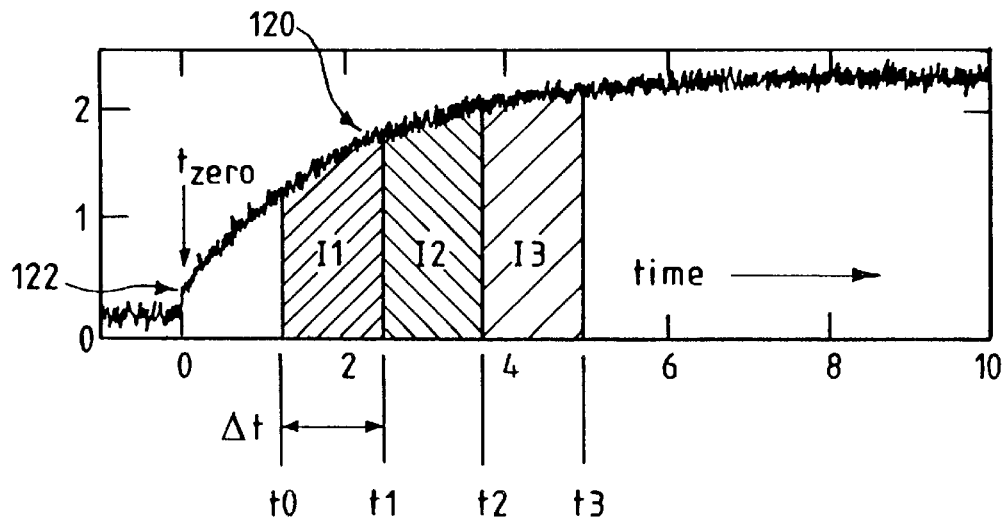
FIG. 5 is diagram of fluorescent activity in a sensor plotted against time during operation of a system embodying the invention.

With reference to the graph FIG. 5, the signal generated by the output of the amplifier stage 72 (and therefore the amount of light reaching the photomultiplier tube 64 from fluorescent activity in the sensor 10) is represented by the line 120. This is plotted against time on the x-axis. In the graph, the LED 40 is energised at $t_{zero}$. The photomultiplier tube detects a small amount of the light from the LED 40 leaking through the beam splitter 46, shown by the step change in level at 122.

Immediately thereafter, the photomultiplier tube 64 begins to detect light emitted by fluorescence in the sensor. This light increases exponentially, resulting in an exponential output from the amplifier stage 72, as represented in FIG. 5.

It has been shown that the lifetime τ of a transient exponential growth can be calculated by integration of the transient curve over three equally-spaced and equal-length time regions.

In the following, I1 represents an integral from time t0 to t1; I2 represents an integral from time t1 to t2; and I3 represents an integral from time t2 to t3. Each of the intervals t1–t0, t2–t1 and t3–t2 is of time Δt. In which case:

$$\tau = \frac{\Delta t}{-\log_e((I2-I3)/(I1-I2))}$$

The initial and the final levels may also be determined from:

$$FinalLevel = \frac{(I1-I2)\log_e(Q)}{\Delta t(1-Q)^2}$$

and $$Initial(t1)Level = \left(I1 - \frac{(I1-I2)/(1-e^{(-\Delta T/\tau)})}{\Delta t}\right) - \frac{(I1-I2)\log_e(Q)}{\Delta t(1-Q)^2}$$

where $$Q = \frac{I2-I3}{I1-I2}$$

In the present embodiment, the integrations required to determine the values of I1, I2 and I3 are performed by the three integrating channels of the integrating stage 76. Furthermore, the integration is performed repeatedly on a multiplicity of energisations of the LED 40 thereby to average the integration value, so as to mitigate the effect of random variations in the integral value which can arise from noise or other sources.

A measurement sequence will now be described in detail with reference being made to FIG. 6.

In FIG. 6, time is represented horizontally. The horizontal lines each represents the variation in time of the logic state of a particular signal line within the system. Each line in FIG. 6 is labelled with a reference numeral which corresponds to the hardware device or signal line described above which is controlled by that signal.

The lower part of FIG. 6 shows a complete measurement cycle. The indicated interval A–B is 1 second.

A measurement cycle is initiated by the control circuit 112 driving the start triggering input line 110 low (active). At the same time, the interrupt line 114 is driven high (inactive). After a delay, the reset line 108 is pulsed to active high, and then brought low again, the falling edge of the pulse arriving exactly one second after the triggering input line 110 was activated.

An acquisition sequence is then started, extending over interval C. Each acquisition sequence comprises a multiplicity of integration sequences, each extending over a variable cycle period shown as D in the upper part of FIG. 6. In the upper part of FIG. 6, there is shown the timing diagram for a minimum-length integration sequence lasting 50 us (upper diagram) and a maximum-length integration sequence lasting 204.8 µs. The number of integration sequences within an acquisition sequence is varied in dependence upon the length of each integration sequence, such that the last integration sequence commences not longer than 900 ms after the start of the acquisition sequence.

Each integration sequence comprises the following steps:

1. At a time L (measured from the start of the integration sequence) the LED control output 98 is driven high, to turn on the LED 40.

2. Between times t0 and t1, the output 100 is driven high to turn on the first channel switch 86; between times t1 and t2, the output 102 is driven high to turn on the second channel switch 86, and between times t1 and t3, the output 104 is driven high to turn on the third channel switch 86. Each channel is switched on for the same length of time Δt (i.e. Δt=t3–t2=t2–t1=t1–t0).

3. After t3, the LED control output 98 is switched off.

4. A delay is imposed (up to the total cycle period D) to allow all fluorescent activity to fully decay.

As the cycle period D is varied, the time interval between L and t0 remains fixed. As the cycle period D is varied, the time interval between L and t0 remains fixed. As Δt is varied, the ratio of LED on-time (L to t3) to the cycle period D remains constant (in this embodiment, at a ratio exceeding 1:8). The principle reason for such variation is to ensure that the three integrations take place over a time period in which the level of fluorescent emission is varying rapidly. It has been found that it is preferable to adjust the cycle period D such that the relationship:

$$0.4\tau \leq \Delta T \leq 2.5\tau$$

is adhered to.

Following this sequence, it will be seen that each of the integration circuits will have performed an integration of the value of the fluorescent activity which corresponds to a respective one of the values of integrals I1, I2 or I3 in the formulae given above.

At the end of the acquisition sequence, the integration will have been performed a multiplicity of times, thereby mitigating the effect of any random fluctuation in the signal received from the photodetector 74. Such fluctuations can result from both electronic noise and from the quantised nature of the photon flux being detected. A measurement sequence E of approximately 100 ms then starts.

In the measurement sequence E, there is first imposed a delay to ensure that the final integration sequence is completed. At the same time, the interrupt line 114 and the control output 106 are then activated to trigger operation of the A/D converter 92, which reads the outputs of the three integrating circuits, and generates a digital value corresponding to each of them. This digital value is then made available to be read by the computer 94.

A time period F before the start of the next acquisition sequence, the reset output 108 is activated to reset the integrating circuits in readiness for the next acquisition cycle.

It will be seen that the computer 94 can then calculate a value for τ by performing only simple arithmetical operations plus a single logarithmic computation. These calculations can readily be performed by a computer of a comparatively modest power within the time interval between successive acquisition sequences. This is in notable contrast to the alternative possibility of using the computer to perform the integration—a process which would require a very substantially longer processing time, such that a very powerful (and expensive) computer would be required to perform such calculations in real time.

Once the value of τ is known, it is readily possible to calculate the percentage concentration of oxygen at the probe tip, by means of the Stern-Volmer relation which specifies that:

$$\frac{\tau}{\tau_0} = 1 + \tau_0 k[O_2]$$

where $\tau_0$ is the lifetime value of the probe in the absence of oxygen.

It should be noted that this ideal relationship is not strictly followed at all oxygen tensions. When the dye is incorporated into a silica/polymer mass, a better approximation of the oxygen tension can be derived by using a form of the Stern-Volmer relation modified to include a Langmuir adsorption isotherm:

$$\frac{\tau}{\tau_0} = 1 + S(N[O_2]/(1 + N[O_2]))$$

where S and N are calibration constants.

Once the computer calculates the value of k, it can display this for immediate reading by an operator, or the value can be processed and stored in any desired manner. For example, the computer may maintain a table of oxygen concentration values, may provide an instantaneous display of oxygen concentration, or drive a plotter to generate a continuous record of the variation in oxygen concentration over time.

Figure 7:
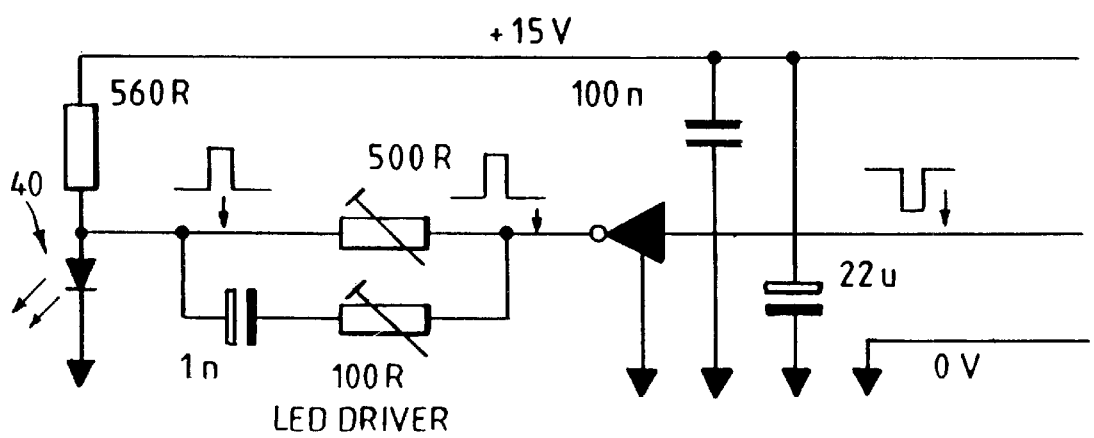
FIG. 7 is a circuit diagram of an electronic switching circuit suitable for fast switching of an LED.

Much of the hardware of the system can be implemented in a straightforward manner. However, care must be taken to ensure that the electronic switches which controls the LED 40 has a fast operating speed to allow the LED to switch on in a time in the order of 30 ns. By this arrangement, an accurate measurement of τ can be obtained. An example of a suitable driver circuit is shown in FIG. 7. As will be understood, the time taken to turn the LED off is not critical. This can extend to the order of a few microseconds.

Although the foregoing description has referred to a sensor for oxygen, the present invention could be applied, in alternative embodiments, to construct sensors for other assay substances by selection of a suitable fluorophor. For example, it is envisaged that hydrogen ion concentration (pH) could be measured using a sulphonic acid anilide or other aromatic hydrocarbon fluorophor, a rhodamine dye, or hydroxypyrenetrisulfonic acid; oxygen concentration could alternatively be measured using a fluoranthene dye, pyrenebutyric acid, polycyclic, homocyclic or heterocyclic aromatic hydrocarbon or lanthanide and/or osmium complexes; carbon dioxide concentration could be measured using β-methylumbelliferone and sodium bicarbonate, and sulphur dioxide or hydrogen peroxide could be detected by means of a fluorophor comprising metal complex in combination with a long-chain alkyl or alkane group ammonium or sulphate ion. It is believed that the invention can also be applied to detection of enzymes using a fluorophor comprising hydrolase oxidases or dehydrogenases of the type of enzyme to be detected. It will be appreciated that the particular formulation of fluorophor required for a particular measuring task can be selected by experimentation in a routine manner by a suitably skilled person.

We claim:

1. A system for measuring the concentration of an assay substance comprising:
    a sensor having a sensing body including a fluorophor, which fluorophor has a fluorescent activity which is measurably altered in relation to the concentration of the assay substance and light conveying means for conveying light to and from the fluorophor;
    a pumping light source which, in operation, applies light to the light conveying means to activate the fluorophor;
    a detector for detecting light emitted by the fluorophor in the polymer body and for generating a signal in response thereto;
    analysing apparatus for analysing the signal generated by the detector, and calculating from that signal the concentration of the assay substance detected by the sensor; wherein
    the detector operates to detect transient change in light emitted by the fluorophor simultaneously with the pumping light source operating to apply light to the optical fibre.

2. A system according to claim 1 wherein the analysing apparatus analyses the increase in the light emitted by the fluorophor which occurs during a period after the pumping light source starts to operate.

3. A system according to claim 1 wherein the light source operates for a time which is substantially longer than the time during which the light emitted by the fluorophor changes following the start of operation of the pumping light source.

4. A system according to claim 1 wherein the pumping light source operates repeatedly, the analysing means being operable to calculate an average value of a plurality of calculated concentration values.

5. A system according to claim 1 wherein the pumping light source and the detector operate to apply light to and receive light from a single light conveying means.

6. A system according to claim 5 further comprising an optical means operative to split light emerging from the light conveying means from the fluorophor from the path of the light entering the optical fibre from the pumping light source.

7. A system according to claim 1 wherein the pumping light source comprises one or more light-emitting diodes.

8. A system according to claim 1 wherein the light conveying means includes one or more optical fibres.

9. A system according to claim 8 wherein the sensor light conveying means includes a single optical fibre which carries light from a pumping light source to the polymer body and which carries light emitted by the fluorophor from the polymer body to a detector.

10. A system according to claim 1 wherein the sensor comprises an optical fibre having an end surface on which is disposed a polymer body within which a multiplicity of particles is immobilised, on which particles is adsorbed the fluorophor, the polymer being such as to allow the assay substance to be absorbed into the body to come into contact with the fluorophor, and the fluorophor being selected as having a fluorescent activity which is measurably altered in the presence of the assay substance.

11. A system according to claim 10 wherein the particles are silica gel particles.

12. A system according to claim 10 wherein the particles have an average diameter of 5 $\mu$m or less.

13. A system according to claim 10 wherein the polymer is a silicone rubber.

14. A system according to claim 9 wherein the optical fibre has a numerical aperture greater than 0.3.

15. A system according to claim 14 wherein the optical fibre has a numerical aperture of greater than 0.4.

16. A system according to claim 15 wherein the optical fibre has a numerical aperture in the range 0.45 to 0.5.

17. A system according to claim 9 wherein the optical fibre has a diameter less than 300 $\mu$m.

18. A system according to claim 17 wherein the optical fibre has a diameter of approximately 200 $\mu$m.

19. A system according to claim 1 wherein the assay substance to which the substance is oxygen.

20. A system according to claim 1 wherein the fluorophor is a ruthenium complex dye.

21. A system according to claim 20 wherein the fluorophor is tris(4,7-diphenyl-1,10-phenanthroline)ruthenium chloride.

22. A system according to claim 1 wherein the fluorophor activity is reduced as the concentration of the assay substance increases.

23. A method of operating a system for measuring the concentration of an assay substance according to claim 1, wherein in an integration sequence:
    (a) the pumping light source is operated to apply light to the light conveying means,
    (b) during operation of the pumping light source, light emitted by the fluorophor is detected as an output of the sensor, and an electrical signal is generated therefrom;
    (c) the signal is processed in order to calculate three or more integration values of the signal integrated over three or more consecutive time periods during a period of exponential rise in the signal;
    in a data acquisition sequence, the integration sequence is performed a multiplicity of times, and three or more sums corresponding to the sums of the integration values are calculated; and
    a time value is calculated from the sums of the integration values, and from that time value, the concentration of the assay substance is determined.

24. An analysis system for calculating a lifetime period of an exponentially varying signal comprising:
    three or more integrating circuits, each having an input for receiving the signal an output on which is generated a signal representative of the value of the input signal integrated over time;
    for each integrator, a switch circuit having a control input and operative to selectively connect or disconnect the input of the associated integrator to the signal in dependance upon the state of its control input;
    timing means responsive to commencement of exponential variation of the signal, and operative in a timing sequence to generate control signals for application to the control inputs of the switch circuits, the control signals being timed such that the three switches connect their respective integrating circuits, in turn, to the signal for three equal and consecutive time periods during exponential change of the signal; and
    computing means operative to receive output signals from the integrating circuits, and perform on them analysis whereby the lifetime value of the exponential change can be determined.

25. An analysis system according to claim 24 wherein the signal is indicative of an intensity of fluorescence in a probe.

26. An analysis system according to claim 24 wherein each integrating circuit includes an operational amplifier integration circuit.

27. An analysis system according claim 24 wherein the computing means comprises a digital computer, the system further comprising an analogue to digital converter to present digital signals to the computer, representative of the output of the integrating circuits.

28. An analysis system according to claim 27 wherein the digital computer is a general-purpose personal microprocessor-based computer.

29. An analysis system according to claim 24 wherein the timing means is operative to send a signal to the computing means to indicate that an integration sequence has been completed and that the output signals of the integration circuits may be analysed.

30. An analysis system according to claim 24 wherein the timing sequence is repeated a multiplicity of times within an integration sequence such that the output signals of the integration circuits represent the sum of the multiplicity of integrations of the input signal.

31. A system for measuring the concentration of an assay substance comprising:
    a sensor having a sensing body including a fluorophor, which fluorophor has a fluorescent activity which is measurably altered in relation to the concentration of the assay substance and light conveying means for conveying light to and from the fluorophor;
    a pumping light source which, in operation, applies light to the light conveying means to activate the fluorophor;
    a detector for detecting light emitted by the fluorophor in the polymer body and for generating a signal in response thereto;
    analysing apparatus for analysing the signal generated by the detector, and calculating from that signal the concentration of the assay substance detected by the sensor; wherein the detector operates to detect light emitted by the fluorophor during a transient period of exponential growth of that light which occurs during a period following the time of which the pumping light source starts to operate; and in that
the analysing apparatus integrates signals generated by the detector to device a period for the exponential growth.

32. A system for measuring the concentration of an assay substance comprising:
a sensor having a sensing body including a fluorophor, which fluorophor has a fluorescent activity which is measurably altered in relation to the concentration of the assay substance and light conveying means for conveying light to and from the fluorophor;
a pumping light source which, in operation, applies light to the light conveying means to activate the fluorophor;
a detector for detecting light emitted by the fluorophor in the polymer body and for generating a signal in response thereto;
analysing apparatus for analysing the signal generated by the detector, and calculating from that signal the concentration of the assay substance detected by the sensor; wherein
the detector operates to detect transient change in light emitted by the fluorophor simultaneously with the pumping light source operating to apply light to the optical fibre; and wherein
the analysing apparatus operates to analyse transient change in the light emitted by the fluorophor simultaneously with activation of the fluorophor with light from the pumping light source.

* * * * *